US010058333B2

(12) United States Patent
Burleigh et al.

(10) Patent No.: US 10,058,333 B2
(45) Date of Patent: Aug. 28, 2018

(54) SURGICAL CLAMP APPARATUS AND A SURGICAL CLAMP FOR USE IN KEYHOLE SURGERY

(71) Applicant: COOK MEDICAL TECHNOLOGIES LLC, Bloomington, IN (US)

(72) Inventors: Tiffany Burleigh, Logan Central (AU); Michael Junger, Brookfield (AU); Andrew Robert Leslie Stevenson, Newport (AU); Anton Lee-See, Camp Hill (AU); James Macnaughtan, Fig Tree Pocket (AU); Cambell Smyth, Highgate Hill (AU); Chris Townsend, Gordon Park (AU)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 149 days.

(21) Appl. No.: 14/785,920

(22) PCT Filed: Apr. 30, 2014

(86) PCT No.: PCT/US2014/036164
§ 371 (c)(1),
(2) Date: Oct. 21, 2015

(87) PCT Pub. No.: WO2014/179460
PCT Pub. Date: Nov. 6, 2014

(65) Prior Publication Data
US 2016/0066917 A1     Mar. 10, 2016

Related U.S. Application Data

(63) Continuation-in-part of application No. 14/189,390, filed on Feb. 25, 2014, now abandoned.

(30) Foreign Application Priority Data

Apr. 30, 2013  (AU) .............................. 2013205730

(51) Int. Cl.
*A61B 17/10* (2006.01)
*A61B 17/128* (2006.01)
(Continued)

(52) U.S. Cl.
CPC .......... *A61B 17/128* (2013.01); *A61B 17/122* (2013.01); *A61B 17/12013* (2013.01);
(Continued)

(58) Field of Classification Search
CPC ....... A61B 17/12; A61B 17/10; A61B 17/122; A61B 17/128; A61B 17/12013
See application file for complete search history.

(56) References Cited

U.S. PATENT DOCUMENTS 5,383,882 A * 1/1995 Buess ............... A61B 17/12013
606/151
6,042,563 A * 3/2000 Morejohn ........ A61B 17/12109
604/164.01
(Continued)

FOREIGN PATENT DOCUMENTS

DE      29823317        5/1998
EP       0117981        1/1984
WO   WO 2009/091313 A1  7/2009

OTHER PUBLICATIONS

International Search Report and Written Opinion for PCT/US2014/036164 dated Oct. 29, 2014, 16 pgs.
(Continued)

*Primary Examiner* — Victor Nguyen
(74) *Attorney, Agent, or Firm* — Brinks Gilson & Lione

(57) ABSTRACT

A surgical clamp assembly 100 for use in keyhole surgery is disclosed. The assembly includes: a surgical clamp 10 for forming a clamping loop around a bodily lumen 8. The clamp includes: a strap 20, the strap including an elongate grippable portion 23; and a head 30 including a gripper 40, (Continued)

the gripper having an open mouth, the open mouth shaped to allow lateral entry of the strap into the gripper so as to form the clamping loop. The assembly further includes: a deployment tube 60 for deploying the clamp through a keyhole; and a manipulator 70 for manipulating the clamp through the deployment tube. The elongate body is biased to move from a constrained generally straight condition within the deployment tube to an unrestrained curled condition within a patient. A surgical clamp assembly, that includes a surgical clamp is also disclosed.

11 Claims, 19 Drawing Sheets

(51) Int. Cl.
*A61B 17/12* (2006.01)
*A61B 17/122* (2006.01)
*A61B 17/00* (2006.01)
*A61B 90/00* (2016.01)

(52) U.S. Cl.
CPC ............... *A61B 2017/00407* (2013.01); *A61B 2017/00455* (2013.01); *A61B 2017/00477* (2013.01); *A61B 2017/00862* (2013.01); *A61B 2017/00867* (2013.01); *A61B 2017/00964* (2013.01); *A61B 2090/038* (2016.02)

(56) References Cited

U.S. PATENT DOCUMENTS

| | | |
|---|---|---|
| 2002/0151955 A1 | 10/2002 | Tran et al. |
| 2008/0208217 A1 | 8/2008 | Adams |
| 2010/0234862 A1 | 9/2010 | Patel et al. |
| 2011/0152900 A1 | 6/2011 | Regadas |

OTHER PUBLICATIONS

Australian Patent Examination Report for related application No. AU 2013205730 dated Feb. 26, 2014, 5 pgs.

* cited by examiner

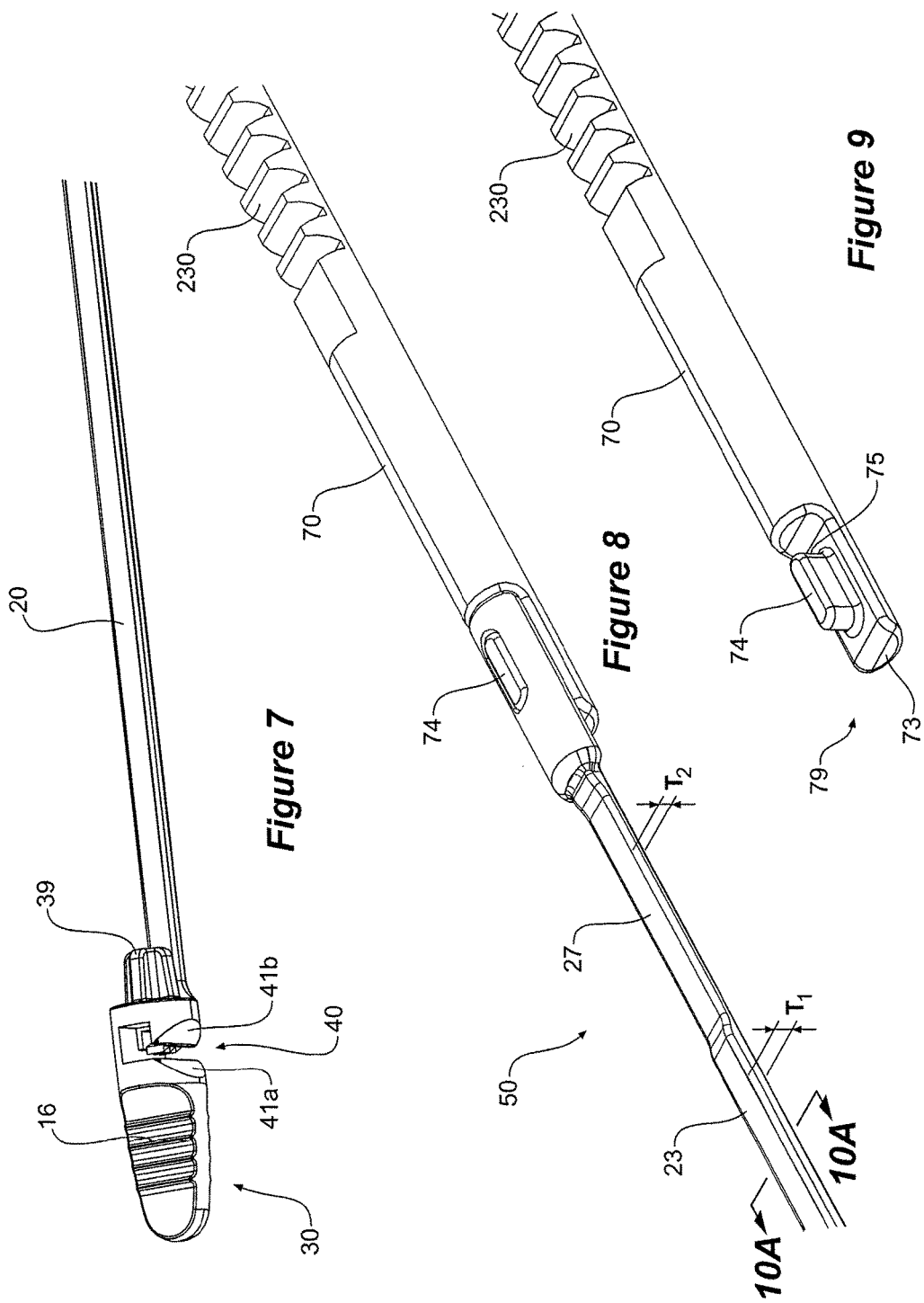

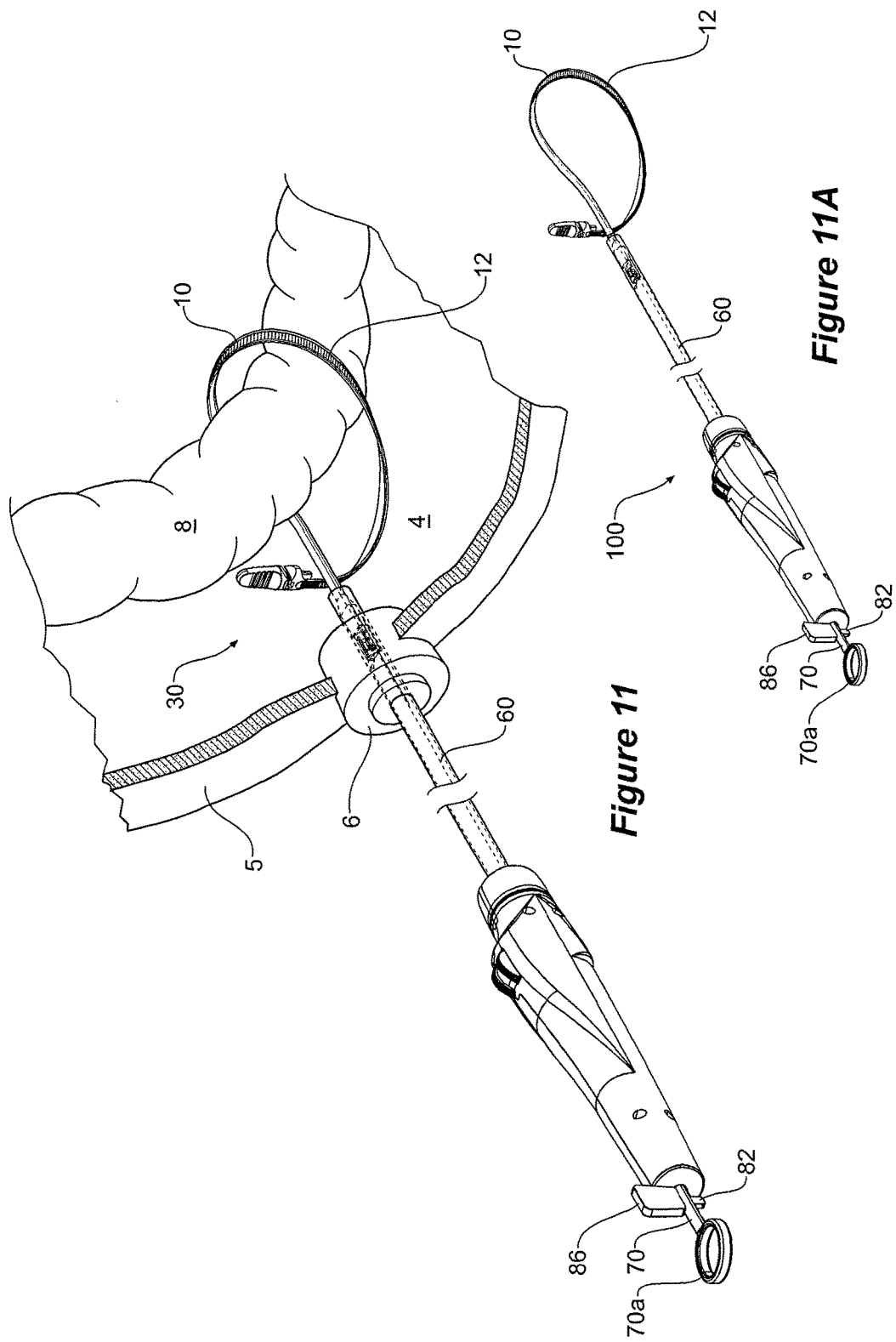

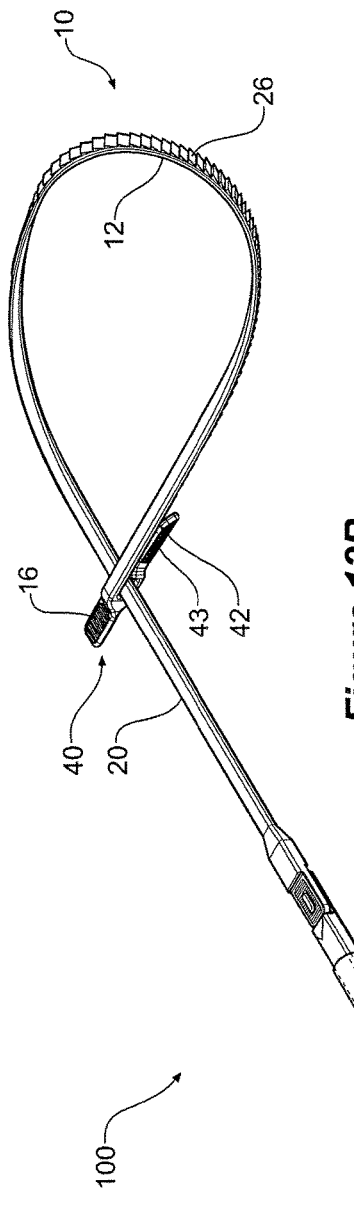
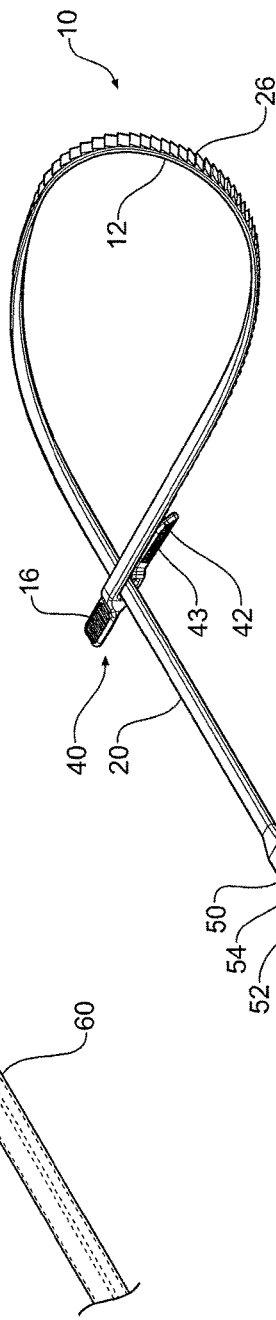
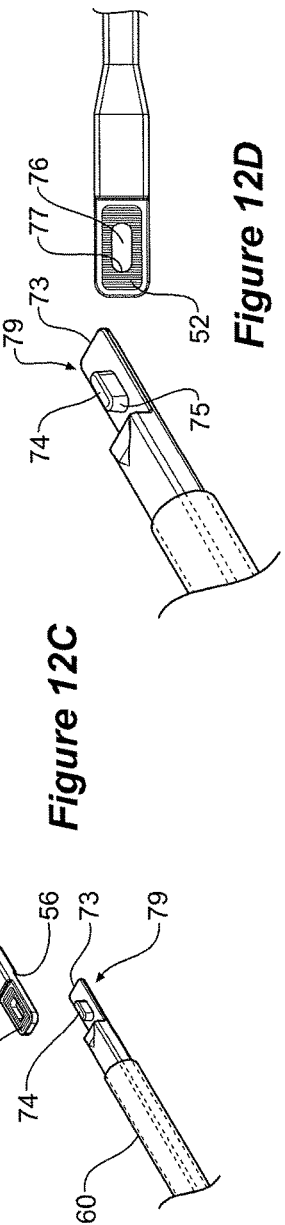
*Figure 12B*
*Figure 12C*
*Figure 12D*

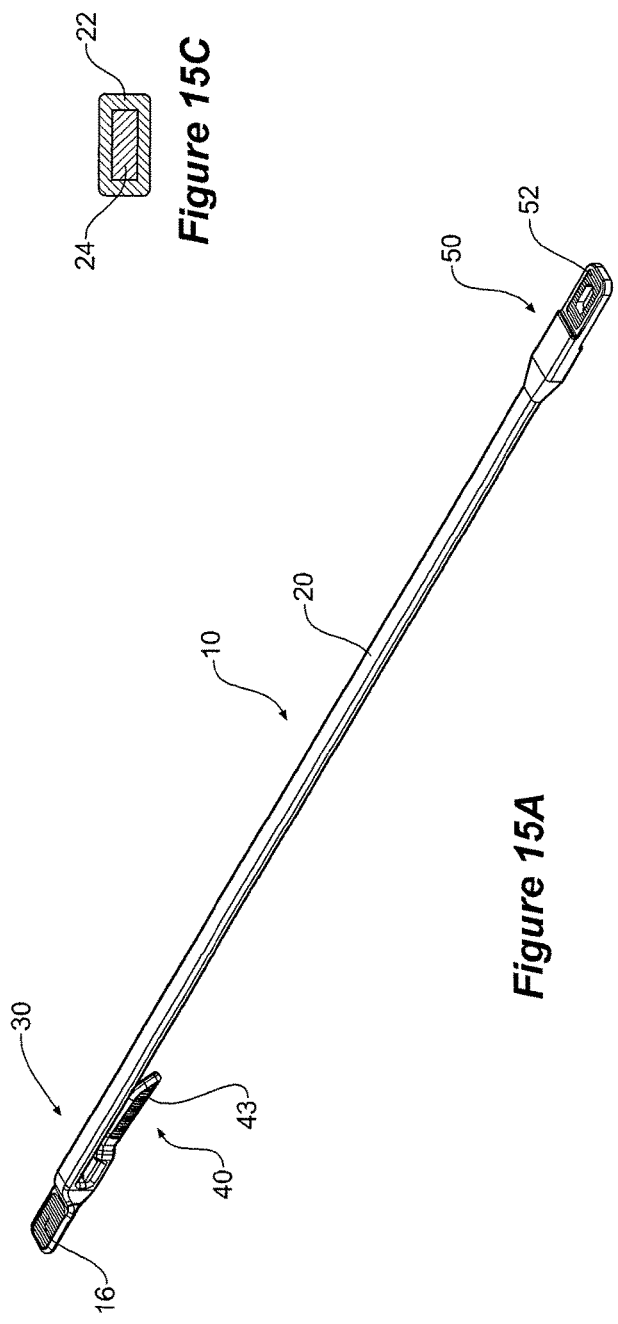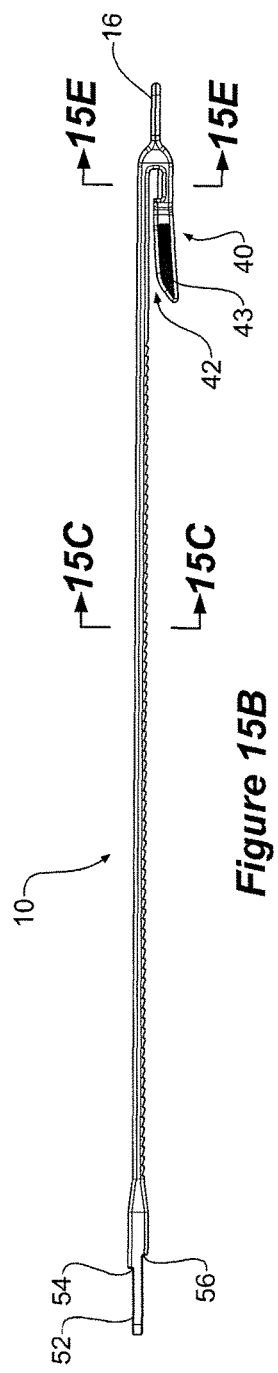

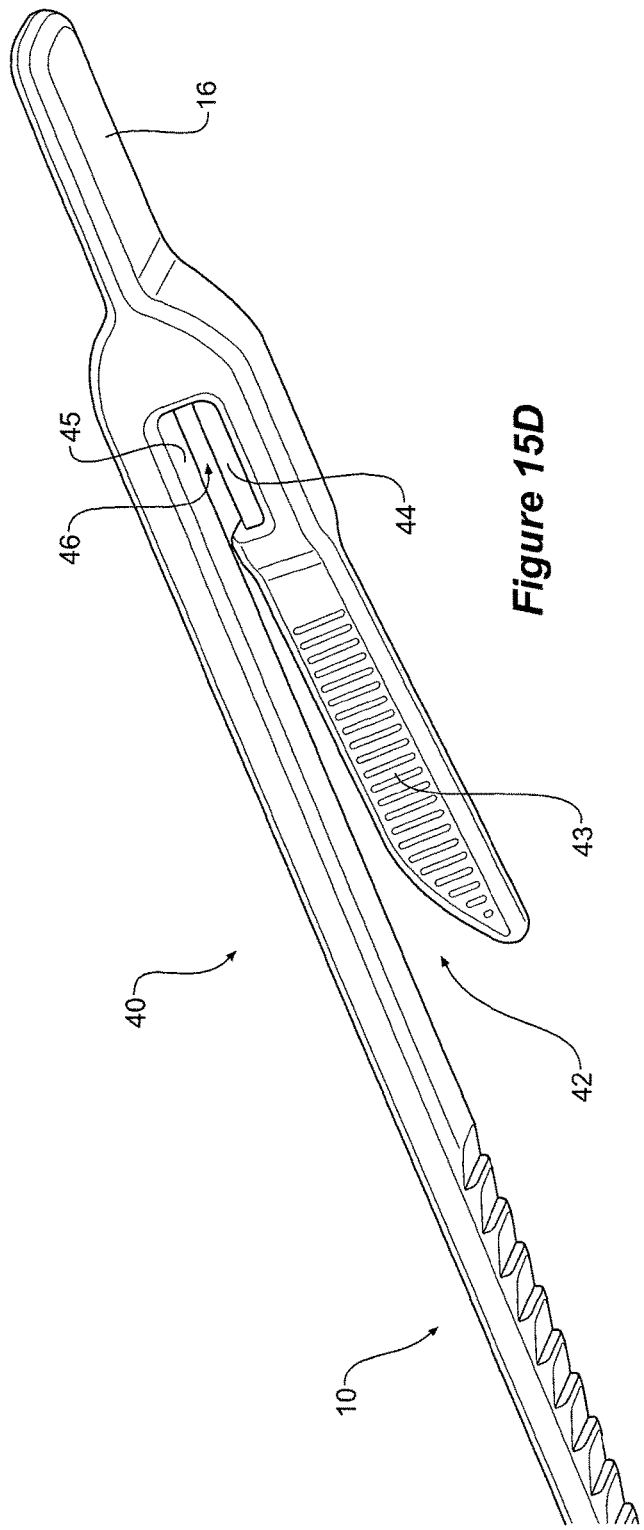
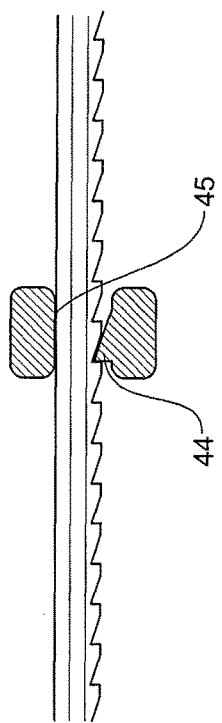

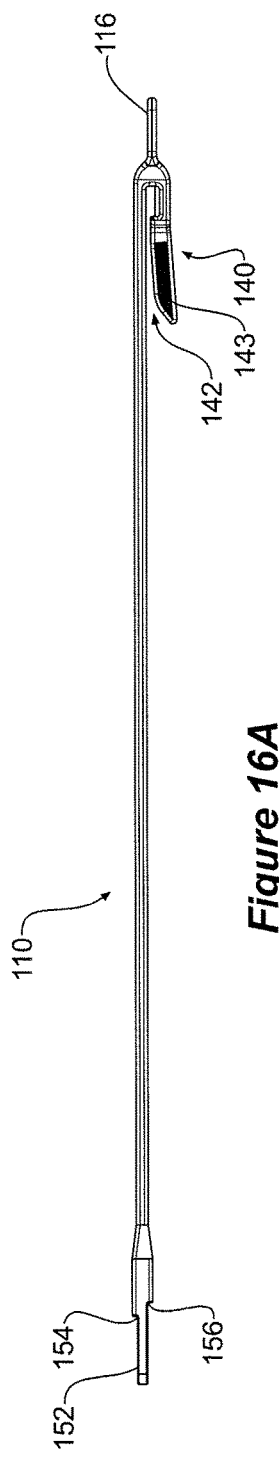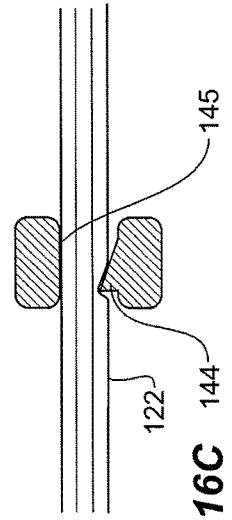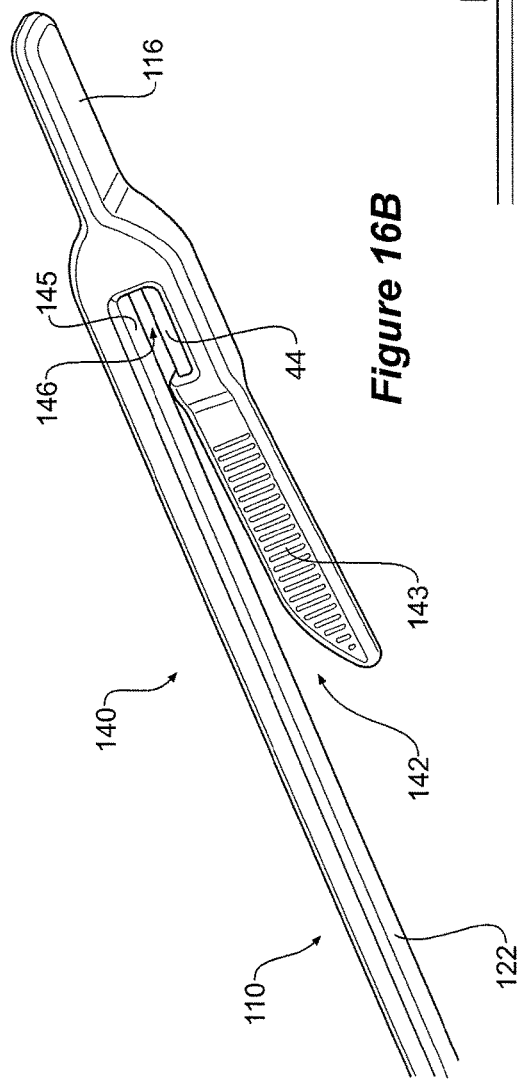

SURGICAL CLAMP APPARATUS AND A SURGICAL CLAMP FOR USE IN KEYHOLE SURGERY

The present patent application is a national phase of PCT Application Number PCT/US2014/036164, filed Apr. 30, 2014, which is a continuation-in-part of U.S. patent application Ser. No. 14/189,390, filed Feb. 25, 2014, and which claims the benefit of the filing date of Australian Patent Application Number 2013205730, entitled "A Surgical Clamp Apparatus and a Surgical Clamp For Use in Keyhole Surgery", the contents of which applications are hereby incorporated by reference.

FIELD OF THE INVENTION

The invention relates generally to medical devices and, in particular, to surgical clamps that are deployable through keyhole surgery.

BACKGROUND OF THE INVENTION

Temporary ligation of a tubular lumen is often required during surgical procedures. For instance, ligation of a bowel lumen, a blood vessel or other bodily lumens, vessels or tubes during surgery may be required. Temporary ligation of lumens is achieved by a number of methods currently. For instance, in gastrointestinal surgery for the resection of colorectal cancer and for the manipulation and retraction of bowel lumen during laparoscopic lower pelvic dissection, surgeons currently use nylon tape or sutures to isolate the lumen. The tape or suture method requires considerable skill and is time consuming.

A further problem with existing ligation tools and methods is that often an additional assistant is required. For instance, an additional assistant may be required during gastrointestinal surgery on females to manipulate the uterus interiorly so as to improve the access and visual operative fields in which the surgeon has to operate in achieving ligation.

It is an object of the present invention to provide a surgical clamp that can be deployed in keyhole surgery that ameliorates at least some of the aforementioned problems or at least offer a useful choice.

SUMMARY OF THE INVENTION

According to the first aspect of the invention, there is provided a surgical clamp assembly for use in keyhole surgery, the assembly including:
 a surgical clamp for forming a clamping loop around a bodily lumen, the clamp including:
  a strap, the strap including an elongate grippable portion; and
  a head including a gripper, the gripper having an open mouth, the open mouth shaped to allow lateral entry of the strap into the gripper so as to form the clamping loop;
 a deployment tube for deploying the clamp through a keyhole; and
 a manipulator for manipulating the clamp through the deployment tube,
 wherein the elongate body is biased to move from a constrained generally straight condition within the deployment tube to an unrestrained curled condition within a patient.

In one form the assembly further includes latching arrangement to latch the clamp to the manipulator.

In one form the latching arrangement comprises a manipulator latch surface on the manipulator co-operable with a tail latch surface on the a tail of the clamp,
 wherein the manipulator latch surface and the tail latch surface remain engaged while the tail latch surface is within the deployment tube and wherein the manipulator and tail latch surfaces readily disengage when the tail latch surface is outside the deployment tube.

In one form the manipulator latch surface is located on a latching projection that projects from the manipulator and the tail latch surface is located within a latching slot within the tail of the clamp.

In one form the latching arrangement co-operates with the deployment tube to form a locking arrangement, the locking arrangement preventing substantial axial movement of the manipulator in a direction axial to the deployment tube and hence preventing unintended release of the clamp.

In one form the assembly further includes a drive assembly for driving the manipulator.

In one form the manipulator includes a manipulator rack and the drive assembly includes a pinion, the pinion engaging the manipulator rack.

In one form the pinion is drivable by a thumb wheel,
 wherein the thumb wheel is adapted to be actuated by an operator's thumb or finger.

In one form the open mouth includes a pair of opposed lead-in surfaces.

In one form the grippable portion of the strap includes a strap rack and the gripper includes a gripper body and a tooth assembly, the tooth assembly engagable with the strap rack.

In one form the tooth assembly is hingedly mounted to the gripper body.

In one form the tooth assembly hinges about a hinge axis, wherein the open mouth opens in a direction parallel to the hinge axis.

In one form the tooth assembly includes a plurality of teeth.

In one form the strap includes a lead-in section, the lead-in section between the grippable portion and the tail, the lead-in section having a thickness T2 and the grippable portion having a thickness T1, wherein T2<T1.

According to a second aspect of the invention, there is provided a surgical clamp for forming a clamping loop around a bodily lumen, the clamp deliverable through keyhole surgery, the clamp including:
 a strap, the strap including an elongate grippable portion;
 a head including a gripper, the gripper having an open mouth the open mouth shaped to allow lateral entry of the strap into the gripper so as to form the clamping loop; and
 a tail, the tail including a tail latch surface, the tail latch surface engagable with a manipulator latch surface,
 wherein the strap joins the tail to the head and wherein the strap is biased to move from a constrained generally straight condition within a delivery device to an unrestrained curled condition within a patient.

In one form the open mouth includes a pair of opposed lead-in surfaces.

In one form the grippable portion of the strap includes a strap rack and the gripper includes a gripper body and a tooth assembly, the tooth assembly engagable with the strap rack.

In one form the tooth assembly is hingedly mounted to the gripper body.

In one form the tooth assembly hinges about a hinge axis, wherein the open mouth opens in a direction parallel to the hinge axis.

In one form the tooth assembly includes a plurality of teeth.

In one form the strap includes a lead-in section, the lead-in section between the grippable portion and the tail, the lead-in section having a thickness T2 and the grippable portion having a thickness T1, wherein T2<T1.

According to a third aspect of the invention, there is provided a surgical clamp for forming a clamping loop around a bodily lumen, the clamp deliverable through keyhole surgery, the clamp including:

an elongate body including an elongate deformable layer having a first hardness and an elongate core having a second hardness, the first hardness less than the second hardness; a leading portion including a gripper, the gripper having an open mouth gripably engageable with the deformable layer to form the clamping loop; and a trailing portion, the elongate body joining the trailing portion to the leading portion, wherein the elongate body is biased to move from a constrained generally straight condition within a delivery device to an unrestrained curled condition within a patient.

In one form the open mouth of the gripper is shaped to allow lateral entry of the elongate body into the gripper.

In one form the open mouth of the gripper is arranged and constructed so as to provide a higher degree of slip resistance against movement of the deformable layer in a direction loosening the clamping loop than the degree of slip resistance against movement of the deformable layer in a direction tightening the clamping loop.

In one form the open mouth includes a tooth and a face opposing the tooth together defining an opening, wherein the opening is sized to grippingly receive the deformable layer.

In one form the tooth is asymmetrically shaped so as to provide the higher degree of slip resistance against movement of the deformable layer in a direction loosening the clamping loop than the degree of slip resistance against movement of the deformable layer in a direction tightening the clamping loop.

In one form the tooth of the mouth is wedge shaped.

In one form the deformable layer has an external shape that defines a series of ratchet teeth, in use the ratchet teeth co-operable with the tooth of the mouth to form a ratchet.

In one form the elongate core is formed from a super elastic material.

A detailed description of embodiments of the invention is provided below along with accompanying figures that illustrate by way of example the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

FIG. 7 is an isometric view of a portion of the surgical clamp shown in FIGS. 6A and 6B;

FIG. 8 is an isometric view of a portion of the surgical clamp of FIGS. 6A and 6B and a portion of a clamp manipulator;

FIG. 9 is an end view of the manipulator shown in FIG. 8;

FIG. 11 is a diagrammatic perspective view showing deployment of the surgical clamp of the invention around a bowel lumen within the abdominal bowel cavity;

FIG. 11A is a diagrammatic perspective view showing storage of the surgical clamp assembly of the invention;

FIGS. 12A, 12B, 12C and 12D are diagrammatic perspective views showing a surgical clamp assembly and surgical clamp according to a further embodiment of the invention;

FIG. 15A is an isometric view of a surgical clamp according to the invention;

FIG. 15B is a side view of the surgical clamp of FIG. 15A;

FIG. 15C is a cross-sectional view through section lines 15C-15C as indicated on FIG. 15B;

FIG. 15D is a close up view of a portion of the surgical clamp shown in FIG. 15A;

FIG. 15E is a cross-sectional view through section lines 15E-15E as indicated on FIG. 15B;

FIGS. 16A, 16B and 16C show an alternative surgical clamp according to the invention in similar views to that of FIGS. 15B, 15D and 15E.

DETAILED DESCRIPTION

Figure 1:
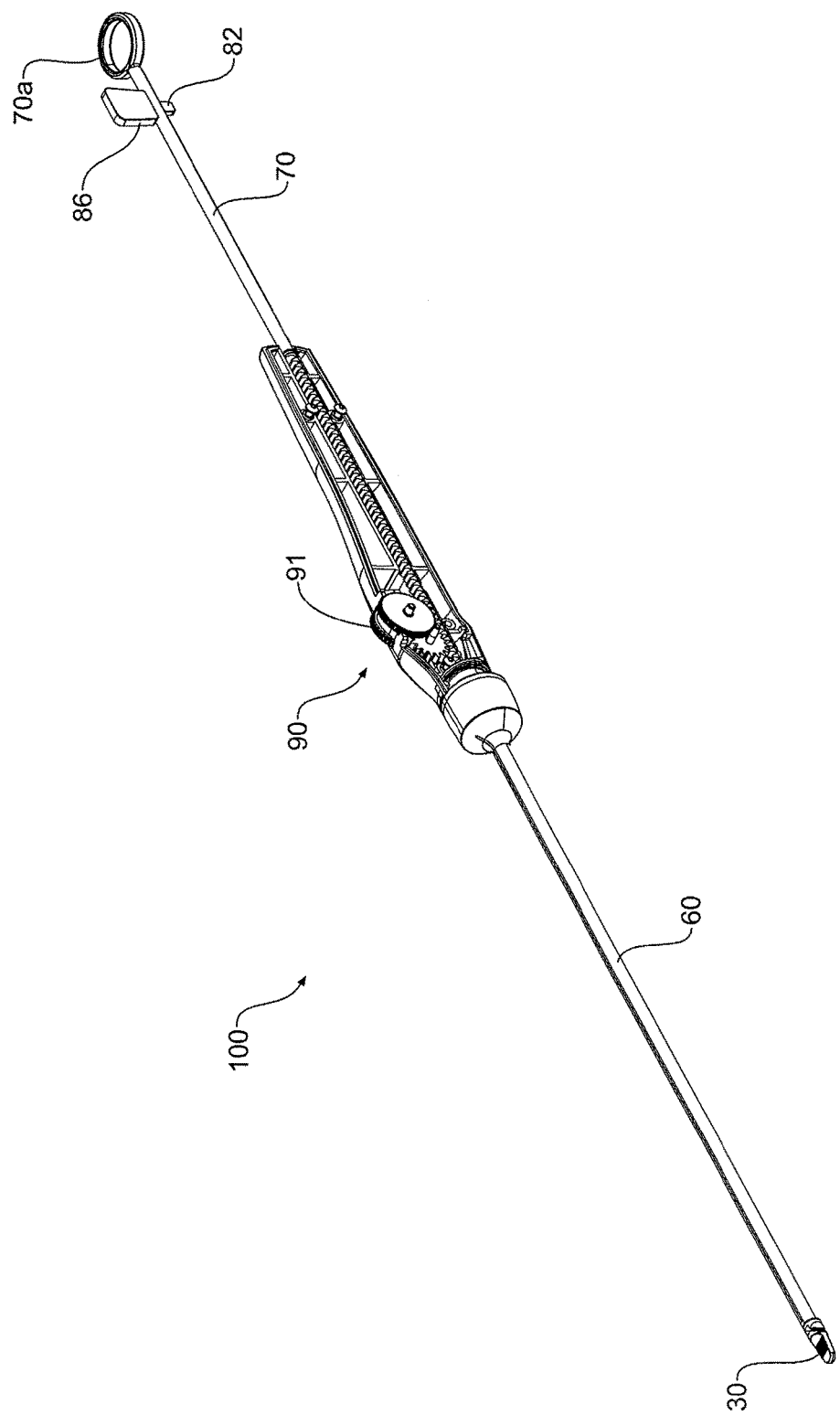
FIG. 1 is a cutaway isometric view showing a surgical clamp assembly and a surgical clamp according to an embodiment of the invention.

FIGS. 1 to 4 shows a surgical clamp assembly according to an embodiment of the invention for use in keyhole surgery. The assembly allows deployment of a surgical clamp through a conventional laparoscopic port 6, as is shown in FIG. 11.

Referring to FIGS. 11 and 11A, the surgical clamp assembly 100 includes a surgical clamp 10 for forming a clamping loop around a bodily lumen (such as a bowel lumen 8), a deployment tube 60 for deploying the clamp 10 through a keyhole and a manipulator 70 for manipulating the clamp through the deployment tube.

Referring to FIG. 11, the surgical clamp 10 can form a clamping loop around a bodily lumen such as the bowel 8 illustrated in FIG. 11. The clamp 10 is more clearly shown in FIGS. 6A and 6B. These figures show that the clamp includes a strap 20, the strap including an elongate grippable portion 23 that is most clearly shown in FIG. 6B. With the embodiment shown in FIG. 6B, the grippable portion 23 of the strap 20 includes a strap rack 26. The clamp 10 also includes a head 30 having a gripper 40. The gripper 40 is more clearly shown in FIG. 7 and in the cross-sectional view of FIG. 10. These figures show that the gripper 40 has an open mouth 42, the open mouth 42 shaped to allow lateral entry of the strap 20 into the gripper 40 so as to form a clamping loop, such as the loop shown in FIG. 11.

Referring to FIGS. 1 to 4, the surgical clamp assembly 100 further includes a deployment tube 60 for deploying the clamp 10 through a keyhole, such as the keyhole shown in FIG. 11. The assembly 100 also includes a manipulator 70 for manipulating the clamp 10 through the deployment tube 60. The strap 20 is biased to move from a constrained generally straight condition within the deployment tube 60 to an unrestrained curled condition within a patient, as is shown in FIG. 11.

With the embodiment shown in FIGS. 1 to 4, a drive assembly 90 is provided for driving the manipulator 70. The drive assembly 90 includes a pinion 92 and a thumb wheel 91. The thumb wheel is adapted to be actuated by an operator's thumb or finger.

Figure 5:
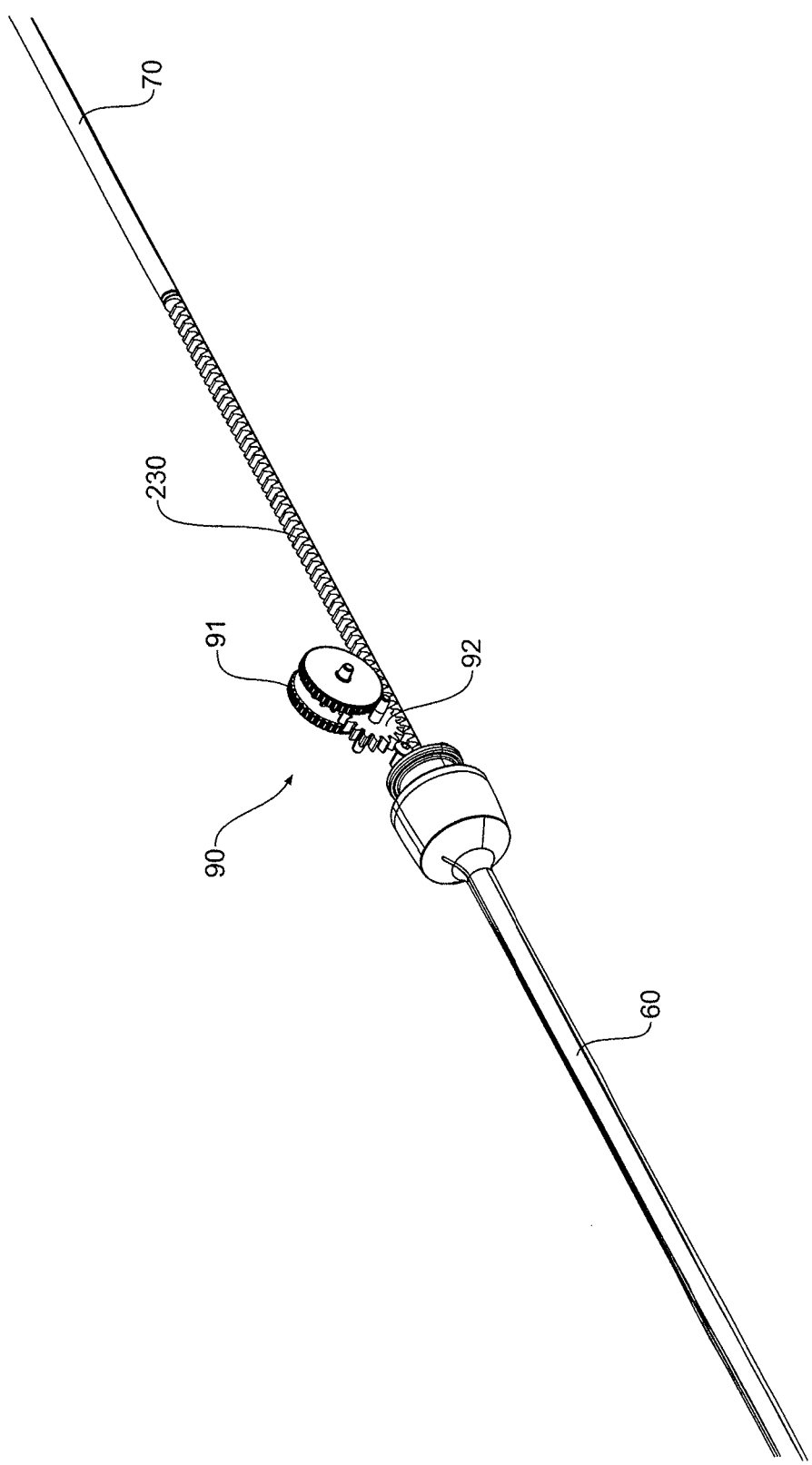
FIG. 5 is a similar view to that of FIG. 1 but shows components removed to provide a better view of internal components.

Referring again to FIG. 5, it can be seen that the manipulator 70 includes a manipulator rack 230 and the pinion 92 of the drive assembly 90 engages with the aforementioned manipulator rack 230. This enables an operator such as a physician to precisely drive the manipulator 70 and hence the clamp 10 out of or into the deployment tube 60.

Figure 2:
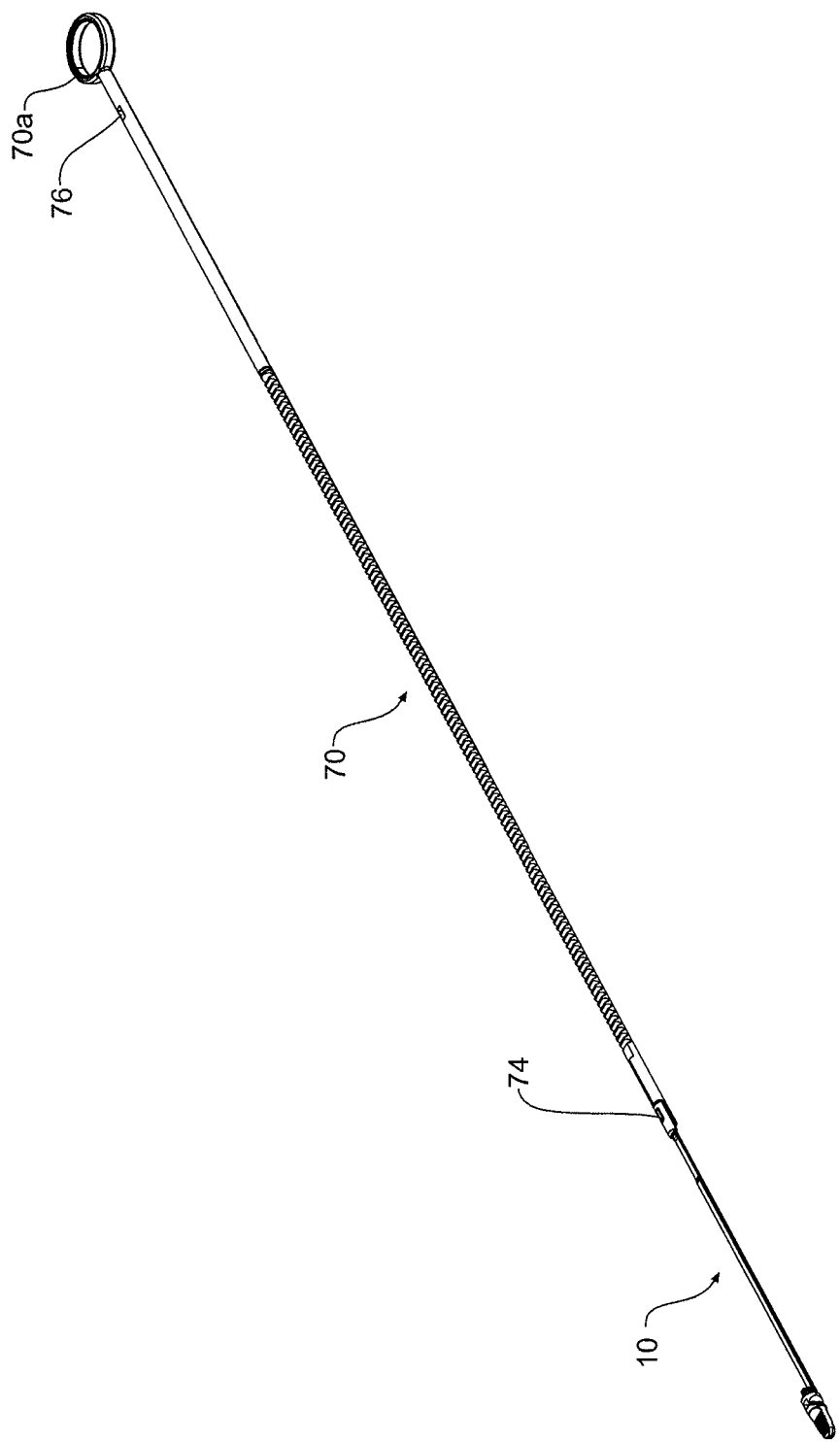
FIG. 2 shows components of the surgical clamp assembly and the surgical clamp of FIG. 1.

Referring now to FIG. 2, it can be seen that the manipulator 70 also has a handle 70a. This handle 70a enables the operator to move the manipulator over larger distances with respect to the deployment tube 60.

Referring now to FIGS. 8 and 9, it can be seen that the clamp 10 has a latching arrangement to latch the clamp 10 to the manipulator 70. The latching arrangement comprises a manipulator latch surface 75 on the manipulator 70 that is co-operable with a tail latch surface 77 on the tail 50 of the clamp 10, as is more clearly shown in FIG. 6B. Referring again to FIG. 8 and FIG. 11, it can be seen that the manipulator latching surface 75 and the tail latching surface 77 remain engaged while the tail latch surface 77 is within the deployment tube 60. Thus, the operator can manipulate the clamp 10 and can decide when to release the tail 50 from the manipulator 70. Once the operator extends the manipulator 70 beyond the position shown in FIG. 11, the tail latch surface 77 moves outside the deployment tube 60 and the manipulator and tail latch surfaces readily disengage. That is, the tail 50 is free to separate from the manipulator 70.

Again referring to FIGS. 6B, 8 and 9, it can be seen that with the embodiment of the invention illustrated, the manipulator latch surface 77 is located on a latching projection 74 that projects from the manipulator 70. The tail latch surface 77 is located within a latching slot 76 within the tail 50 of the clamp 10.

As should be clear from the above, the latching arrangement co-operates with the deployment tube 60 to form a locking arrangement. The locking arrangement prevents substantial axial movement of the manipulator 70 in a direction axial to the deployment tube 60 and hence prevents unintentional release of the clamp 10.

The tail latch surface 75 is rounded on one side to ensure the clamp 10 is loaded on the correct way (i.e. one way fit). This ensures that the clamp 10 (being either the first or a second clamp 10) will always deploy and curl out in the same direction.

Figure 6A:
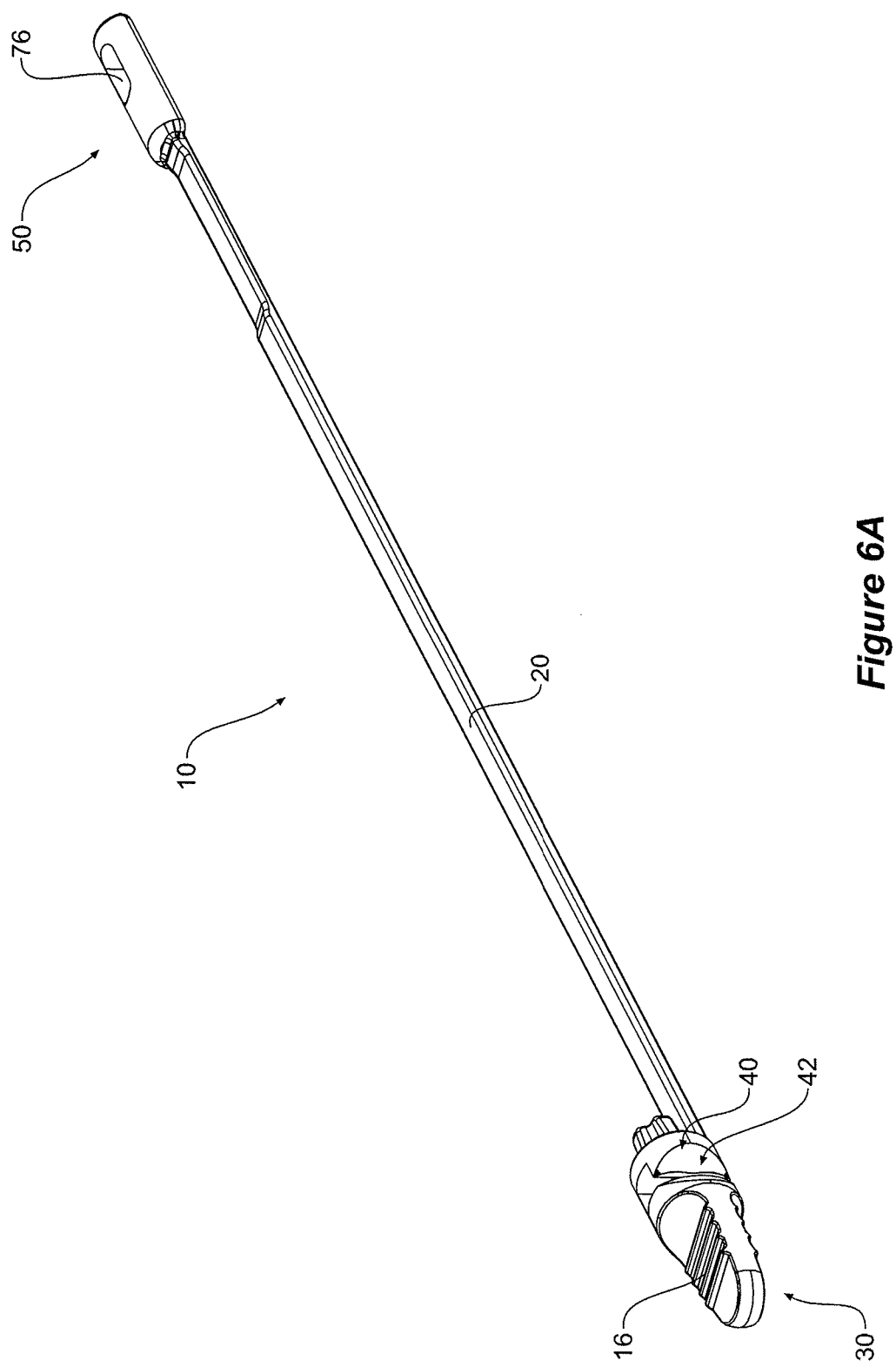
FIGS. 6A and 6B are isometric views of a surgical clamp according to an embodiment of the invention.
Figure 6B:
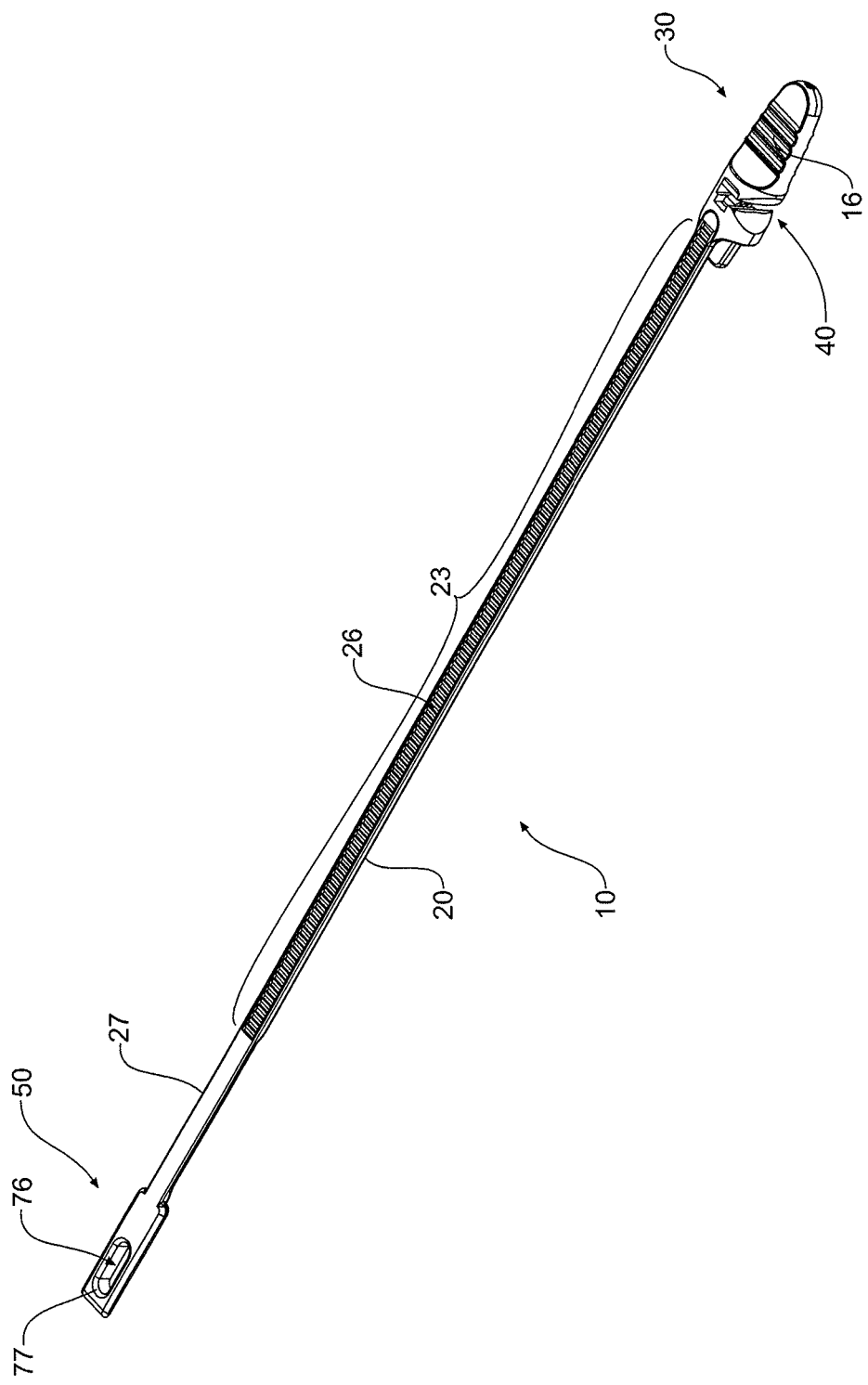
Figure 10A:
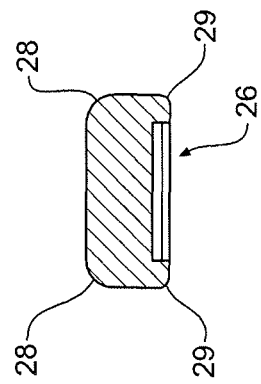
FIG. 10A is a cross-sectional view of the strap of the surgical clamp of FIGS. 6A and 6B.
Figure 10:
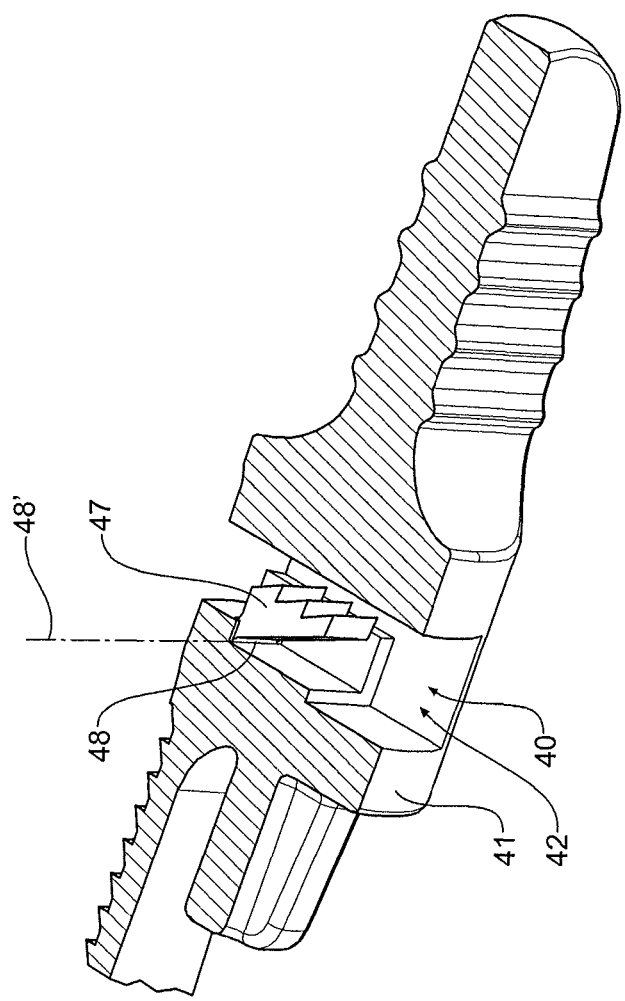
FIG. 10 is a cross-sectional view of a head component of the surgical clamp of FIGS. 6A and 6B.

Referring now to FIG. 6B and FIG. 10, the clamp 10 will be described in more detail. As can be seen from FIG. 10, the open mouth 42 of the head 30 includes a pair of opposed lead-in surfaces 41a and 41b, as is most clearly shown in FIG. 7.

As can be seen in FIG. 6B, the grippable portion 23 has a strap 20 that includes a strap rack 26 and the gripper 40 includes a gripper body 41 and a tooth assembly 47 that is most clearly shown in FIG. 10. The tooth assembly 47 is engageable with the strap rack 26. The tooth assembly 47 is hingably mounted to the gripper body 41 to allow hinging about a hinge axis 48'. Again referring to FIG. 10, it can be seen that the open mouth 42 opens in a direction parallel to the hinge axis 48'.

With the embodiment illustrated in FIGS. 7 and 10, the tooth assembly 47 includes three teeth. In other embodiments, not shown, one, two, four or more teeth may be used.

Again referring to FIG. 6B, it can be seen that the strap 20 of the clamp 10 includes a lead-in section 27. The lead-in section 27 is located between the grippable portion 23 and the tail 50. The grippable portion has a thickness T1 and the lead-in section 27 has a thickness T2, as is most easily seen in FIG. 8. The thickness T2 is less than the thickness T1 of the grippable portion. This facilitates lead-in, or in other words, directing the strap 27 into the open mouth 42 of the gripper 40.

While a lead-in section 27 is provided with the embodiment illustrated, the gripper 40 is designed to also allow lateral entry of the grippable portion 23 of the strap 20. Furthermore, the strap is designed such that release of the grippable portion from the tooth assembly 47 is possible by lateral movement of the grippable portion 23 back out of the open mouth 42.

The edges 28, 29 of the strap 20 are rounded so as to be atraumatic for the clamped bowel. This reduces the risk of cutting through a lumen such as the bowel when the clamp is done up tight for occlusion.

The rounded shape of the cross-section of the strap at the grippable portion, as shown in FIG. 10A, also facilitates lateral entry of the grippable portion 23 into the open mouth. As FIG. 10A shows, the grippable portion has rounded edges 29 adjacent to the rack 26. The rounded edges 29 allow the grippable portion to wedge against the teeth of the tooth assembly 47 so as to induce them to pivot about their hinge axis 48' thereby making room for the grippable portion.

Referring to FIG. 1, it can be seen that a pin 82 having a pin handle 86 is provided. The pin 82 passes through a slot 76 within the manipulator 70 (the slot 76 is most clearly shown in FIG. 2). The pin 82 is provided to prevent premature deployment of the clamp 10. The pin 82 and the slot 86 limit axial movement of the manipulator 70 in a direction axial to the deployment tube 60 and therefore prevents unintended release of the clamp 10 from the manipulator 70. In other embodiments of the invention, alternatives may be used to prevent unintended release of the clamp 10 from the manipulator 70. For instance, a patterned or coloured surfaced may be provided to provide a visual indication of the point of no return.

With the embodiment of the clamp 10 shown in FIGS. 6A and 6B, all of the components of the clamp 10 are formed from plastic in a unitary construction. Many plastics suffer from creep. Therefore, with the embodiment of the invention illustrated in FIGS. 1, 2 and 4, the surgical clamp assembly 100 is packaged and stored as is shown in FIG. 11A. That is, the clamp 10 is mostly outside of the tube 60 and rests in a curled state. This reduces the likelihood of creep occurring. Before use, an operator is able to pull the handle 78a so as to retract the clamp 10 into the deployment tube 60 to the position shown in FIG. 3.

The surgical clamp 10 according to another embodiment of the invention is shown in FIGS. 15A, 15B and 15C. Referring to these figures, it can be seen that the surgical clamp 10 includes an elongate body 20, a leading portion or head 30 that includes a gripper 40 and a trailing portion or tail 50. The elongate body 20 joins the trailing portion 50 to the leading portion 30. The elongate body 20 includes an elongate deformable layer 22 and an elongate core 24 shown most clearly in the cross-sectional view of FIG. 15C taken through section lines 15C-15C shown in FIG. 15B.

Figure 17:
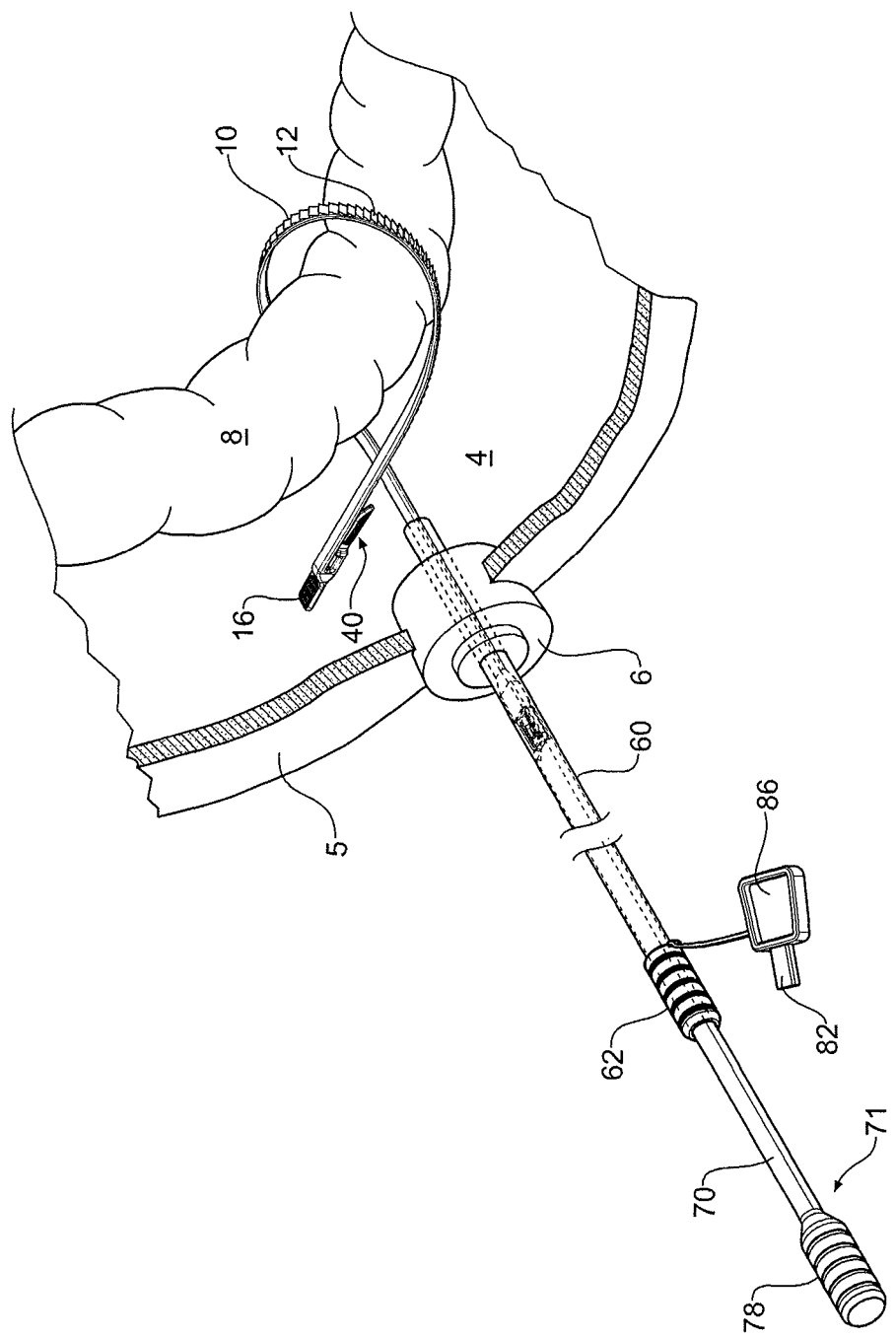
FIG. 17 is a diagrammatic perspective view showing deployment of a surgical clamp of the invention around a bowel lumen within the abdominal bowel cavity.

The gripper 40 of the leading portion 30 has an open mouth 42, as shown in FIGS. 15B and 15D. The open mouth 42 is shaped to allow lateral entry of the elongate body 20 into the gripper. The open mouth 42 is grippably engageable with the deformable layer 22 to form a clamping loop, as is illustrated in FIGS. 15E and 17.

FIG. 15A shows the surgical clamp 10 in an extended approximately linear condition for clarity. While the clamp 10 sits in this condition within the deployment tube 60, as shown in FIGS. 13A and 13B, it is biased to move from this generally straight condition, constrained within the tube 60, to an unrestrained curled condition within a patient such as is shown in FIG. 17. More specifically, the surgical clamp 10 is biased such that it will curl around its target lumen, such as a bowel or blood vessel, as it is deployed, as is shown in FIG. 17. When fully deployed, the gripper 40 is substantially aligned with the elongate body 20 as can be seen in FIGS. 12B and 12C.

The gripper 40 on the clamp 10 will now be described in more detail with reference to FIGS. 15B, 15D and 15E. The open mouth 42 of the gripper 40 is arranged and constructed so as to provide a higher degree of slip resistance against movement of the deformable layer in a direction loosening the clamping loop 12 than the degree of slip resistance against movement of the deformable layer in a direction tightening the clamping loop 12 (shown in FIGS. 12A-12C). More specifically, the open mouth 42 includes a tooth 44 and a face 45 opposing the tooth 44 as is most clearly shown in FIG. 15E. The tooth 44 and face 45 together define an opening 46 as shown in FIG. 15D, wherein the opening 46 is sized to grippingly receive the deformable layer 22. A mouth tab 43 also forms part of the gripper 40. The mouth tab 43 is grippable by a standard surgical gripper and allows the surgeon to manipulate the mouth tab 43 so as to loosen or remove the clamp 10.

The tooth 44 is asymmetrically shaped so as to provide the higher degree of slip resistance against movement of the deformable layer in the direction of loosening the clamping loop 12 than the degree of slip resistance against movement of the deformable layer in a direction tightening the clamping loop 12. It can be seen from the cross-sectional view of FIG. 15E that the tooth is wedged shaped.

The elongate core 24 of the clamp 10 can be formed from a super elastic material. For instance, Nitinol. The deformable layer 22 of the clamp 10 can be formed from silicon. The silicon may be over moulded over the Nitinol strip. The trailing portion 50 and the leading portion 30 of the clamp 10 may have the same Nitinol core but may be over moulded with alternative plastics such as polycarbonate, polypropylene or similar materials. The leading portion 30 includes a leading tab 16 suitable for gripping with a surgical gripper as shown in FIG. 15A. Similarly, a trailing tab 52 is provided at the trailing portion 50 of the clamp 10. Again, the trailing tab is suitable for gripping with a surgical gripper. The leading and trailing tabs allow a surgeon to readily manoeuvre the clamp 10 during a procedure.

Figure 12A:
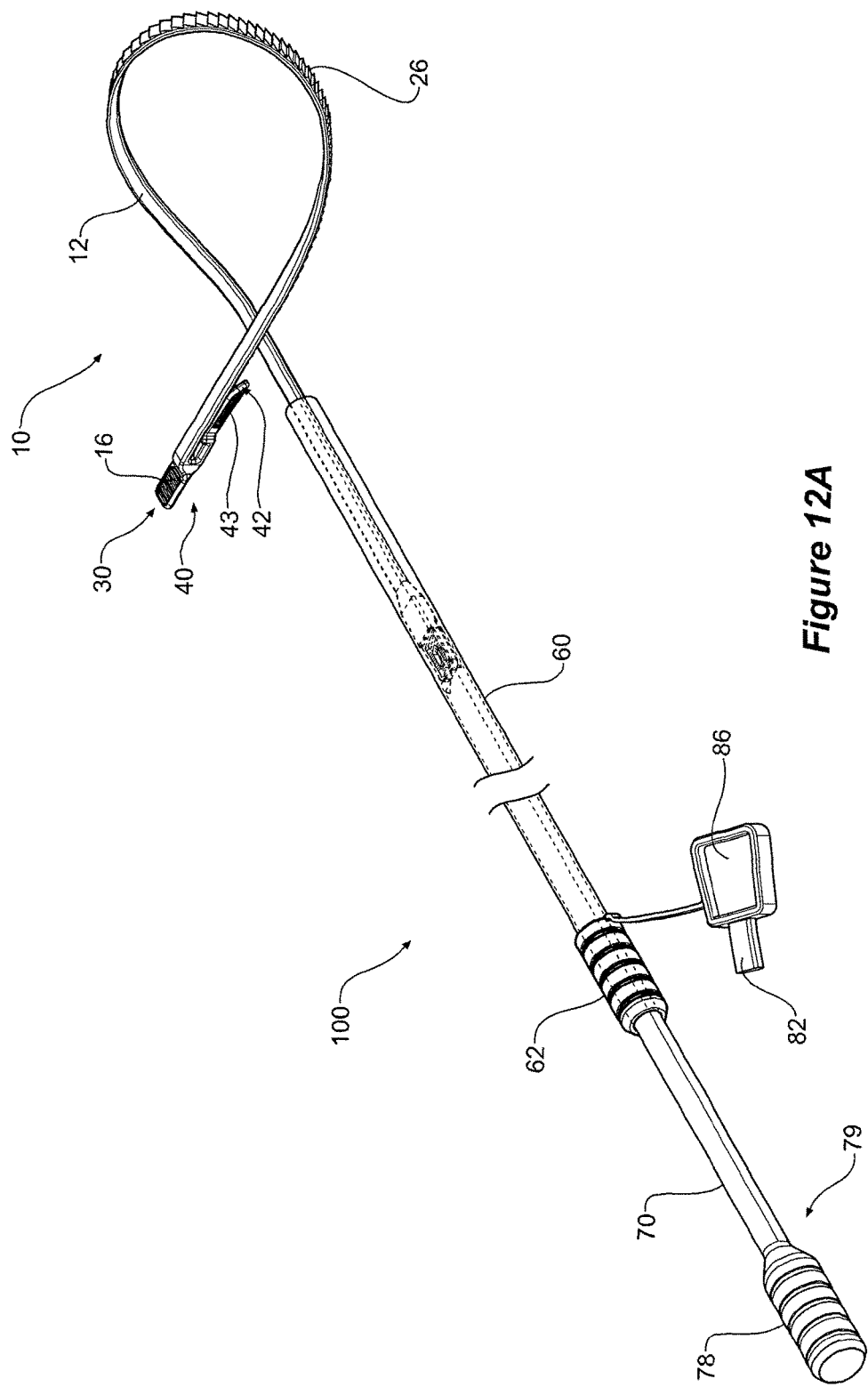
Figure 13A:
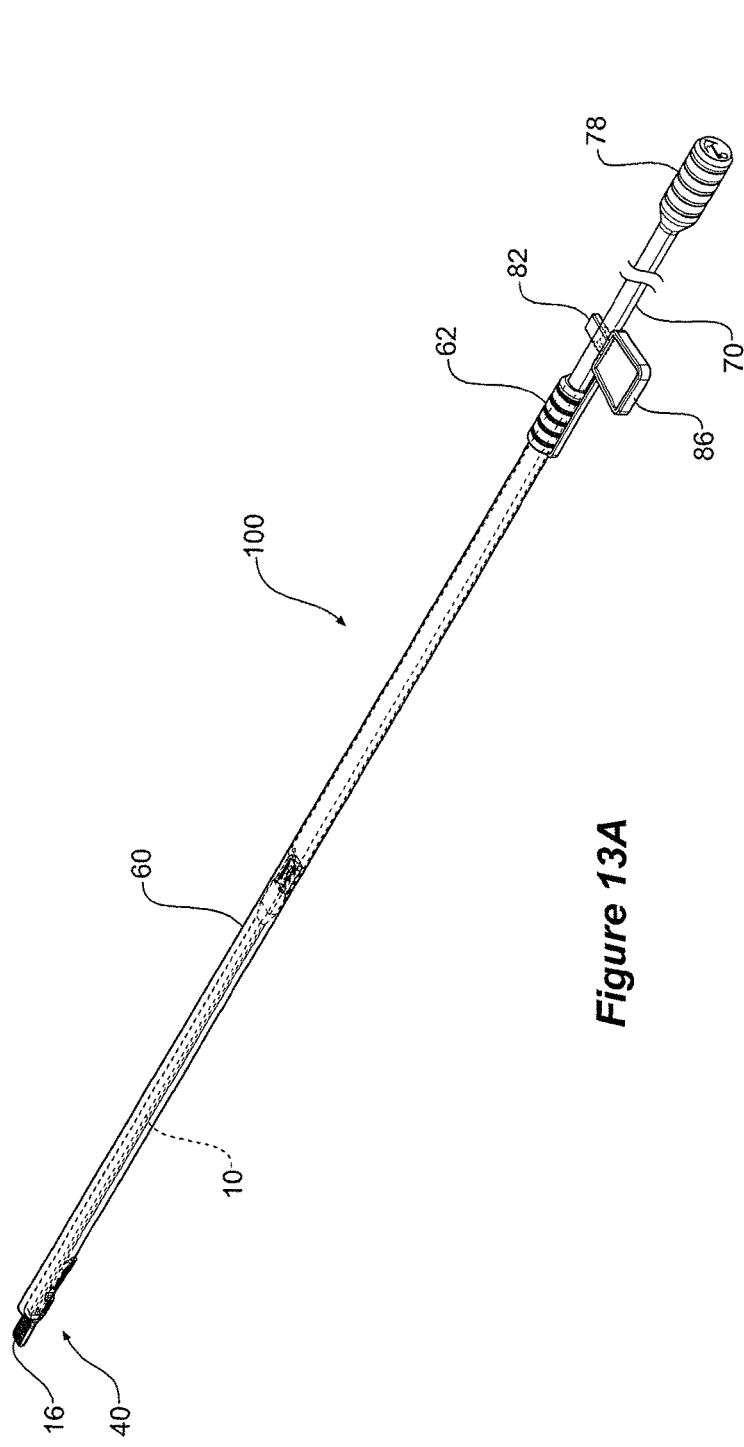
FIG. 13A is an isometric view of the surgical clamp assembly of FIG. 12A.
Figure 13B:
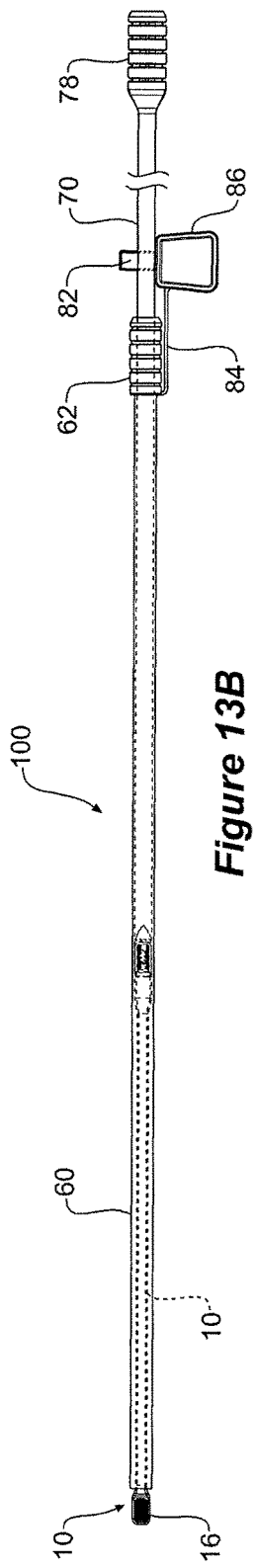
FIG. 13B is a side view of the assembly of FIG. 13A.

The surgical clamp assembly 100 of FIG. 12 includes a latching arrangement to latch the clamp 10 to the manipulator 70. The latching arrangement is shown in FIGS. 12A, 12B, 12C and 12D. FIG. 12C shows the distal end 79 of the manipulator 70 extended out through the end of the deployment tube 60. It can be seen from FIGS. 12C and 12D that the distal end 79 of the manipulator has a latching projection 74 that has a latching surface 75 for engagement with a corresponding latching surface 77 inside a latching slot 76 within the clamp 10 as is most clearly shown at FIG. 12D.

Referring to FIGS. 12C and 12D, it can be seen that the trailing portion 50 of the clamp has shoulders 54 and 56 on opposing sides. The shoulders are sized such that the trailing portion 50 can only fit onto the projection 74 at the end of the manipulator 70 one way. If an attempt is made to assemble the surgical clamp assembly 100 with the clamp 10 upside down, as compared to that shown in FIG. 12C, the end 73 of the manipulator 70 will not align with the shoulder 54. This prevents incorrect assembly.

Referring to FIGS. 12A, 12B and 12C, it can be seen that the latching surfaces 75 and 77 remain engaged while the latching surface 77 remains inside the deployment tube 60. Once the manipulator has been extended out from the deployment tube 60, as is shown in FIG. 12B, the clamp 10 can release from the manipulator 70.

Referring again to FIGS. 13A, 13B and 13C, it can be seen that the surgical clamp assembly 100 has an arrangement 80 to prevent premature deployment of the clamp 10. The locking arrangement 80 prevents substantial axial movement of the manipulator 70 in a direction axial to the deployment tube 60 and therefore prevents unintended release of the clamp 10 from the manipulator 70. The arrangement 80 comprises a pin 82 engaged in a slot 76 within the manipulator 70 and a pin retainer 84. The pin 82 prevents substantial movement of the manipulator 70 in a direction axial to the deployment tube 60. The arrangement 80 is shown more clearly in FIG. 13C. It can be seen that the pin 82 has a grippable handle 86. The tube 60 has an end piece 62 and a pin retainer 84 which extends between the tube end piece 62 and the pin handle 86. The pin retainer 84 is a connecting means that prevents the pin 82, once removed, from dropping. The pin retainer 84 and end piece 62 are molded as a single component.

Figure 13C:
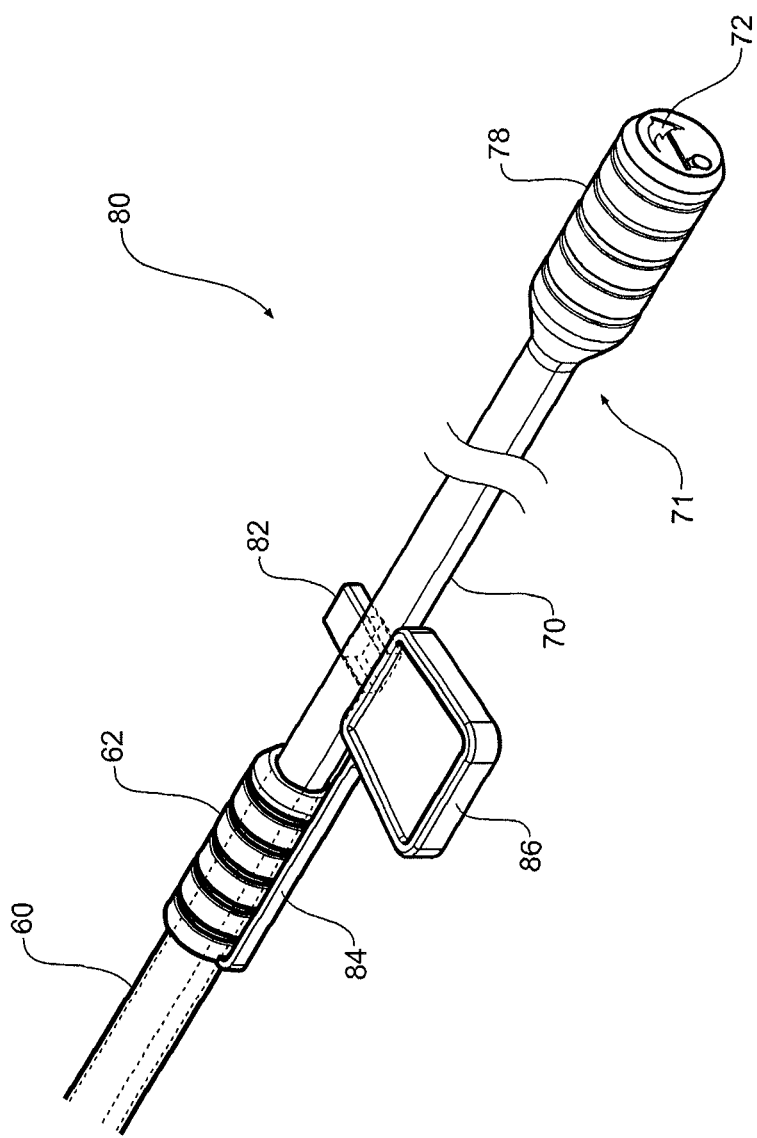
FIG. 13C is a close up view of a portion of the clamp assembly shown in FIG. 13A.
Figure 14A:
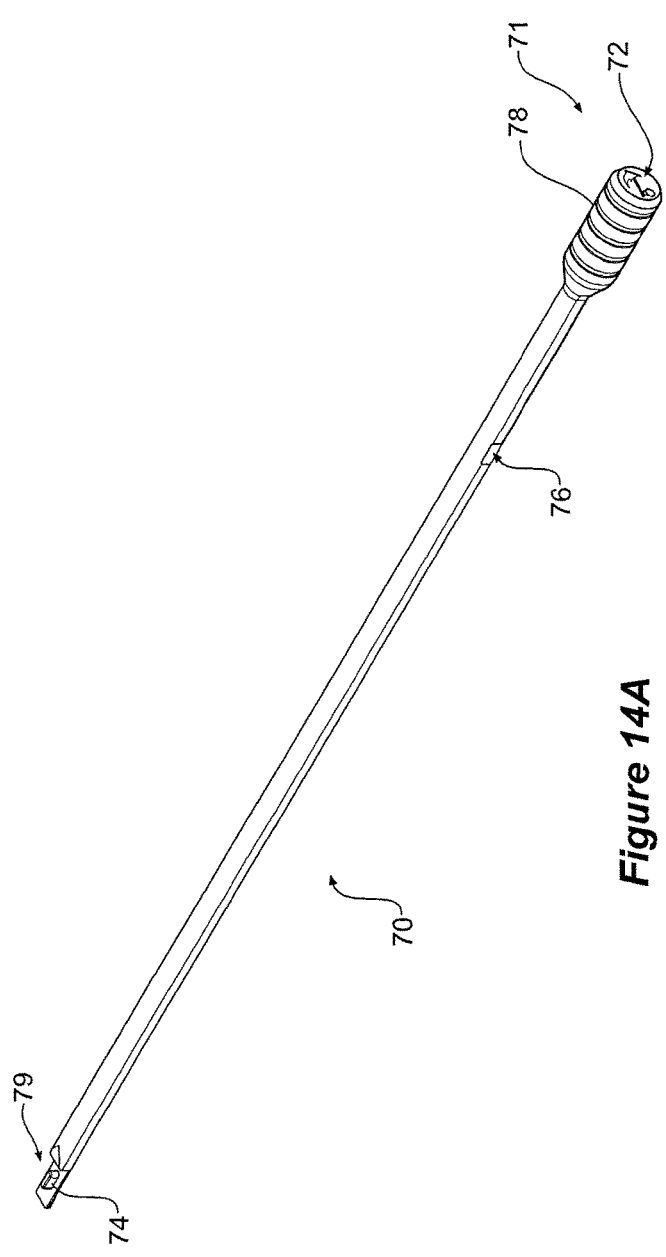
FIG. 14A is an isometric view of a manipulator that forms part of the clamp assembly of FIG. 13A.
Figure 14B:
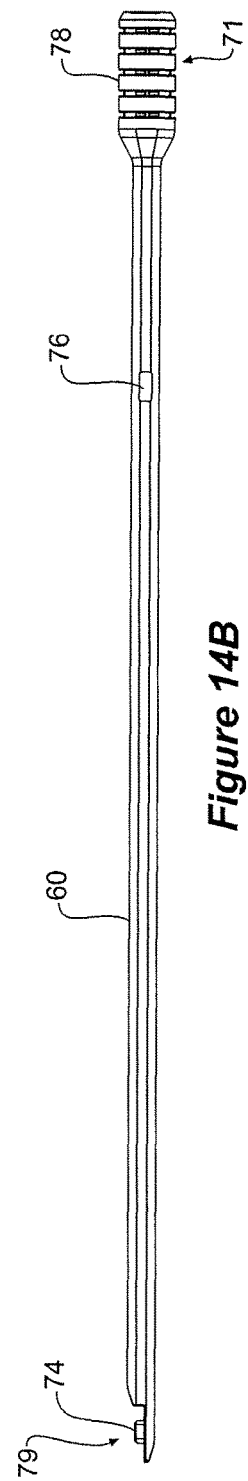
FIG. 14B is a side view of the manipulator of FIG. 14A.

FIG. 13C also shows an arrow symbol on the proximal end 71 of the manipulator 70. The arrow symbol 72 is provided to indicate to the surgeon the deployment direction for the clamp 10.

As can be seen in FIG. 15B, the deformable layer 22 of the clamp 10 has an external shape that defines a series of ratchet teeth. The ratchet teeth co-operates with the tooth 42 to form a ratchet. FIGS. 16A, 16B and 16C show an alternative embodiment of the invention. The clamp 110 is similar to the clamp 10 shown in FIG. 15B but the deformable layer 122 is smooth and flat. It is locally deformed by the tooth 144 within the gripper 140. Other embodiments, not shown, may have deformable layers with a combination of teeth serrations and smooth sections for instance.

Operation of the surgical clamp assembly 100 will now be described with reference to FIGS. 1 to 11A.

The surgical clamp assembly 100 will typically be provided to a hospital in the configuration illustrated in FIG. 11A. Before surgery, an operator retracts the clamp 10 into the deployment tube 60, for instance, by pulling the handle 70a to the position shown in FIG. 3. The head tail 39, shown in FIG. 7, engages with the tube 60 so as to minimise lateral movement of the head 30 with respect to the deployment tube 60. The clamp 10 is now in a generally straight condition but retains a bias towards the curled position shown in FIGS. 11 and 11A. As FIG. 3 shows, the surgical clamp is now housed primarily within the deployment tube 60.

The surgical clamp 10 is latched to the manipulator 70, as is shown in FIG. 8. A pin 82 that passes through a slot within the manipulator 70 limits axial movement of the manipulator 70 in the deployment tube 60. This, in turn, limits axial movement of the clamp 10 with respect to the deployment tube 60 and prevents premature release of the end 73 of the clamp 10.

Figure 3:
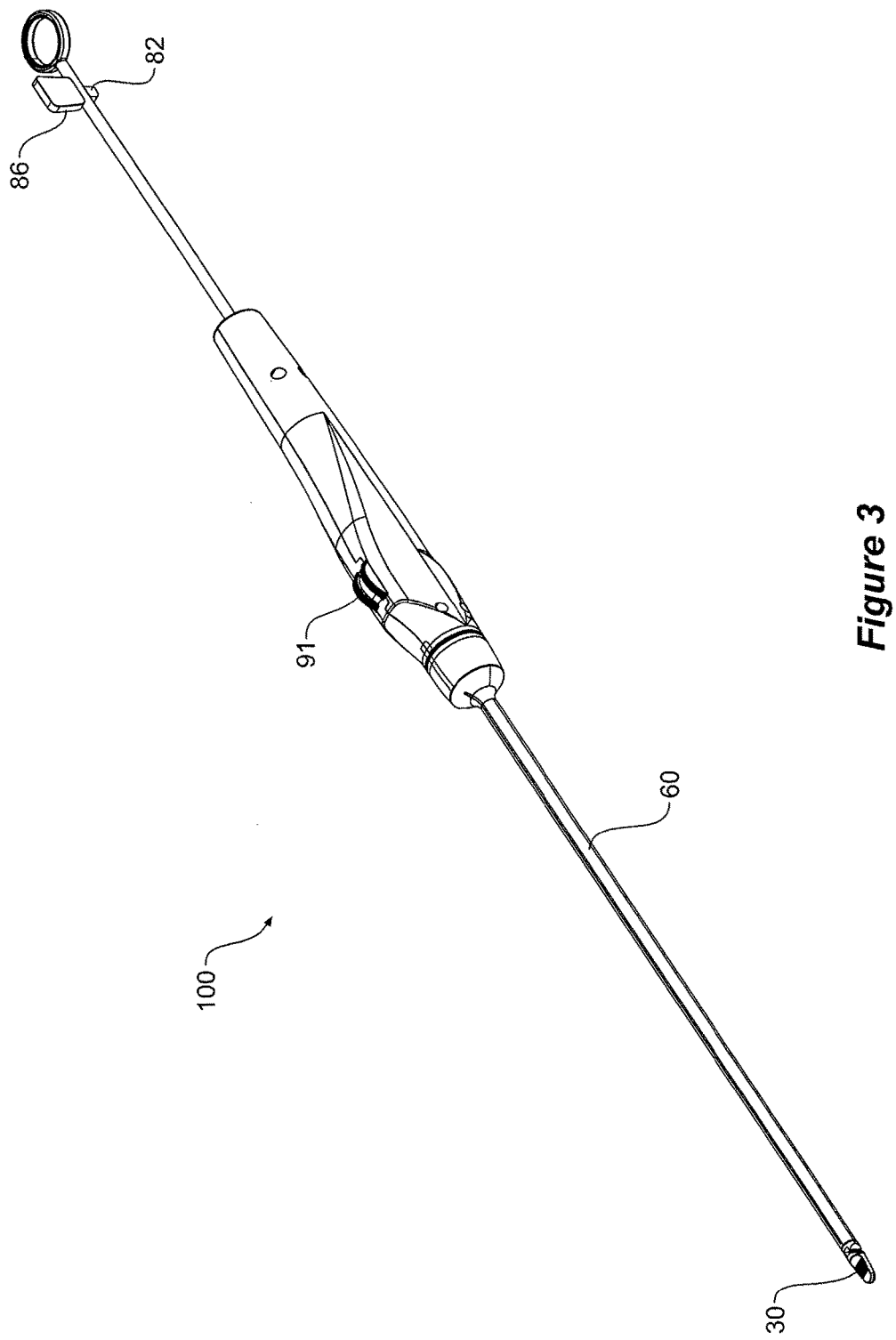
FIG. 3 is an isometric view showing the surgical clamp assembly and the surgical clamp of FIG. 1.
Figure 4:
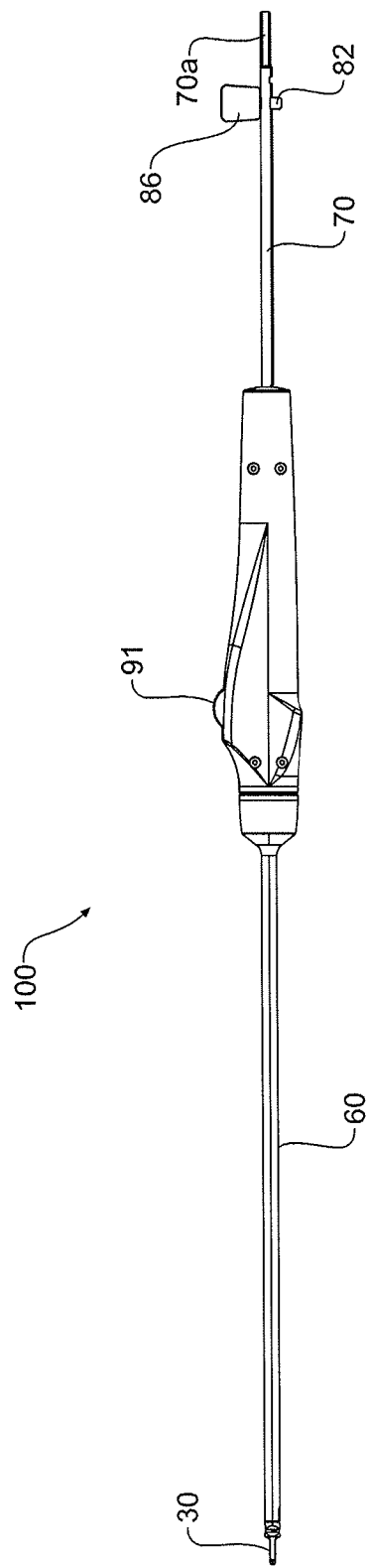
FIG. 4 is a side view showing the surgical clamp assembly and the surgical clamp of FIG. 1.

A surgeon then takes the assembly 100 as illustrated in FIGS. 1, 3 and 4 and inserts it through a conventional laparoscopic port 6, such as is diagrammatically illustrated in FIG. 11. This enables the surgeon to access a bodily cavity 4 from a position external to the body of the patient.

Through manipulation of the handle 78, the surgeon can control the deployment of the clamp 10 such that it curls around a bodily lumen, such as a bowel 8 that is shown in FIG. 11. As described previously, the clamp 10 is biased to curl into the position shown in FIG. 11. If necessary, the surgeon may grip the leading tab 16 at the leading end of the clamp 10 in order to assist in circling the bowel 8. The open mouth 42 of the gripper 40 facilitates easy lateral entry of the elongate body 20 of the clamp 10 into the gripper 40. The gripper 40 is also designed such that the surgeon can easily loosen or release its grip on the elongate body 20. The operator can use the drive assembly 90, as described above, for fine movement of the clamp 10 with respect to the deployment tube 60. He or she may operate the drive assembly 90 using his or her finger or thumb, for instance.

When the surgeon is ready to release the clamp 10, he/she removes the pin 82 using the pin handle 86 from the slot 76 within the manipulator 70. He/she is then able to drive the manipulator 70 sufficiently far so as to push the end 73 out of the tube 60. Once the end 73 is out of the tube 60, it will readily release from the projection 74.

After the clamp 10 has been deployed around the bowel 8 for instance, the manipulator 70 can be re-loaded with another clamp 10 of the type shown in FIGS. 6A and 6B.

Use or operation of the surgical clamp assembly 100 of the alternative embodiment shown in FIG. 12 is similar to the operation described above. However, with the assembly shown in FIGS. 12A to 12D, an indicator arrow 72, best shown in FIG. 13C, is provided to show the orientation of the clamp 100.

When the surgeon wishes to release the clamp 10 from the deployment tube 60, he/she slides the handle 78 of the manipulator 70 all the way in until it contacts the end tubing piece 62. FIG. 12B shows this position at the proximal end of the deployment tube 60. As is shown progressively in FIGS. 12B and 12C, in this position, the clamp 10 is able to release from the manipulator 70.

The positioning of the latching slot 76 and pin 82 are different in the embodiments shown in FIGS. 1 to 5 on the one hand and FIGS. 12A to 12D on the other hand. The usage of such pins and slots or other retaining/latching means may be changed to suit particular requirements. For instance, the positioning such that limited movement between the manipulator and the tube can occur, such as is shown in FIGS. 1 to 6, may be used in relation to the embodiment shown in FIGS. 12A to 12D.

While the clamps 10 may be used as part of the surgical clamp assembly 100 as described above, alternatively it may be used on its own. For instance, the clamps 10 may be used in open surgery without the delivery system.

The embodiments of the invention described above reduce the skill required to feed the clamp around the vessel and/or to tie it off. It also provides a less traumatic closure than a suture.

Throughout this specification, the term distal with respect to the deployment device or prosthesis means the end of the deployment device or the prosthesis further away in the direction from the patient, while the deployment device or the prosthesis is in use, and the term proximal means the portion of the deployment device or the prosthesis nearer to the patient, while the deployment device or the prosthesis is in use.

It is to be understood that the above described embodiments of the invention are merely illustrative of the principals of this invention and that other surgical clamping assemblies and surgical clamps may be devised by those skilled in the art without departing from the spirit and scope of this invention.

It is to be understood that the term "comprise" and any of its derivatives (eg. comprises, comprising) as used in this specification and the below claims is to be taken to be inclusive of features to which it refers, and is not meant to exclude the presence of any additional features unless otherwise stated or implied.

The invention claimed is:

1. A surgical clamp assembly for use in keyhole surgery, the assembly including
   (A) a surgical clamp for forming a clamping loop around a bodily lumen, the surgical clamp including:
   a strap, the strap including a tail, an elongate grippable portion and a lead-in section, the lead-in section positioned between a first end of the grippable portion and the tail, the lead-in section having a thickness T2 and the grippable portion having a thickness TI, wherein T2<T1; and
   a head positioned at a second end of the grippable portion and including a gripper, the gripper having an open mouth the open mouth shaped to allow lateral entry of the strap into the gripper so as to form the clamping loop;
   (B) a deployment tube for deploying the clamp through a keyhole;
   (C) a manipulator for manipulating the clamp through the deployment tube, and
   (D) a latching arrangement positioned to latch the clamp to the manipulator wherein the elongate grippable portion is biased to move from a constrained generally straight condition within the deployment tube to an unrestrained curled condition within a patient.

2. The assembly as claimed in claim 1 wherein the latching arrangement comprises a manipulator latch surface on the manipulator co-operable with a tail latch surface on the a tail of the clamp, wherein the manipulator latch surface and the tail latch surface remain engaged while the tail latch surface is within the deployment tube and wherein the manipulator and tail latch surfaces readily disengage when the tail latch surface is outside the deployment tube.

3. The assembly as claimed in claim 2 wherein the manipulator latch surface is located on a latching projection that projects from the manipulator and the tail latch surface is located within a latching slot within the tail of the clamp.

4. The assembly as claimed in claim 3 wherein the latching arrangement co-operates with the deployment tube to form a locking arrangement, the locking arrangement preventing substantial axial movement of the manipulator in a direction axial to the deployment tube and hence preventing unintended release of the clamp.

5. The assembly as claimed in claim 4 including a drive assembly for driving the manipulator.

6. The assembly as claimed in claim 5 wherein the pinion is drivable by a thumb wheel, wherein the thumb wheel is adapted to be actuated by an operator's thumb or finger.

7. The assembly as claimed in claim 4 wherein the manipulator includes a manipulator rack and the drive assembly includes a pinion, the pinion engaging the manipulator rack.

8. The surgical clamp of claim 1 wherein the open mouth includes a pair of opposed lead-in surfaces.

9. The surgical clamp of claim 1 wherein the grippable portion of the strap includes a strap rack and the gripper includes a gripper body and a tooth assembly, the tooth assembly engagable with the strap rack.

10. The surgical clamp of claim 9, wherein the tooth assembly is hingedly mounted to the gripper body.

11. The surgical clamp of claim 9, wherein the tooth assembly hinges about a hinge axis, wherein the open mouth opens in a direction parallel to the hinge axis.

\* \* \* \* \*